United States Patent [19]

Banks

[11] 4,454,368

[45] Jun. 12, 1984

[54] OLEFIN METATHESIS AND CATALYST

[75] Inventor: Robert L. Banks, Bartlesville, Okla.

[73] Assignee: Phillips Petroleum Company, Bartlesville, Okla.

[21] Appl. No.: 506,950

[22] Filed: Jun. 22, 1983

[51] Int. Cl.$^3$ .............................................. C07C 6/00
[52] U.S. Cl. .................................... 585/646; 585/647
[58] Field of Search ................................ 585/646, 647

[56] References Cited

U.S. PATENT DOCUMENTS

| | | | |
|---|---|---|---|
| 3,642,931 | 2/1972 | Turner et al. | 260/683 D |
| 3,658,927 | 4/1972 | Crain et al. | 260/666 A |
| 3,676,520 | 7/1972 | Heckelsberg | 585/647 |
| 3,723,563 | 3/1973 | Bradshaw | 260/683 D |
| 3,981,940 | 9/1976 | Zuech | 585/646 |
| 4,078,013 | 3/1978 | Blewett et al. | 585/646 |
| 4,262,156 | 4/1981 | Banasiak | 585/646 |

*Primary Examiner*—Curtis R. Davis

[57] ABSTRACT

Olefins are converted into other olefins having different numbers of carbon atoms by contact with a catalyst produced by contacting an inorganic refractory oxide support containing rhenium oxide with a promoting amount of at least one aluminum alkyl and, optionally, at least one tin alkyl compound under conditions suitable for aluminum and tin alkyl compounds to promote the activity of the rhenium oxide for the disproportionation reaction.

16 Claims, No Drawings

OLEFIN METATHESIS AND CATALYST

BACKGROUND OF INVENTION

This invention relates to the disproportionation (metathesis) of olefins. In accordance with one aspect, this invention relates to a catalyst suitable for use in the disproportionation of acyclic olefinic hydrocarbons. In accordance with another aspect, this invention relates to a process for the disproportionation of acyclic olefinic hydrocarbons. In accordance with a further aspect, this invention relates to a catalyst suitable for use in the disproportionation of acyclic olefins comprising rhenium oxide, a support and at least one aluminum alkyl compound. In accordance with a further aspect, this invention relates to a catalyst suitable for use in the disproportionation of acyclic olefins comprising rhenium oxide promoted with at least one aluminum alkyl compound and at least one tin alkyl compound. In accordance with another aspect, this invention relates to a process for the disproportionation of acyclic olefinic hydrocarbons with a disproportionation catalyst as hereinbefore described under conditions of temperature and pressure which effect disproportionation of the feed.

The disproportionation, or metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene and cis-, and trans-2-butene. Another type of disproportionation involves the co-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having lower and higher carbon numbers than the feed hydrocarbons.

Among the catalysts that have been developed for disproportionation are those comprising inorganic, refractory oxides containing a catalytic amount of rhenium oxide. The present invention is based upon the discovery of a way to improve the activity of such a catalyst.

Accordingly, an object of this invention is to provide a method for the conversion of olefins.

Another object of this invention is to provide a catalyst for the conversion of olefins.

Still another object of this invention is to provide a method for converting olefins to similar olefins of higher and lower numbers of carbon atoms.

Still another object is to provide a method for improving the activity of a rhenium catalyst for the conversion of olefins into similar olefins of higher and lower numbers of carbon atoms.

Other aspects, objects and the several advantages of the invention will be apparent to one skilled in the art upon reading the disclosure including a detailed description of the invention and the appended claims.

SUMMARY OF INVENTION

In accordance with the present invention, a disproportionation (metathesis) catalyst comprising an inorganic refractory oxide containing a catalytically effective amount of rhenium oxide is improved by contacting the catalyst with a promoting amount of at least one aluminum alkyl compound under conditions suitable for the aluminum alkyl to promote the activity of rhenium oxide.

Further, in accordance with the present invention, a disproportionation (metathesis) catalyst comprising an inorganic refractory oxide containing a catalytic amount of rhenium oxide is improved by contacting the rhenium oxide catalyst with a promoting amount of at least one aluminum alkyl compound and at least one tin alkyl compound under conditions suitable for the aluminum alkyl and tin alkyl compounds to promote the activity of rhenium oxide.

Also according to the invention, a process is provided for the disproportionation of an acyclic olefinic hydrocarbon by contacting the same with a disproportionation catalyst as hereinbefore described under conditions of temperature and pressure which effect disproportionation of the feed.

DESCRIPTION OF PREFERRED EMBODIMENTS

Inorganic refractory oxide supports that can be used include solid inorganic oxides comprising Group IVB metal oxides such as a titanium dioxide and zirconium dioxide. Titanium dioxide is presently preferred as the support.

Rhenium oxide can be combined with the support in any conventional manner such as dry mixing, impregnation from a diluent, ion exchange or the like. The oxides can be added directly or in the form of rhenium compounds that can be converted to oxides by calcination. Calcination is conducted by heating the impregnated support in the presence of an oxygen-containing gas, such as air, under conditions sufficient to convert the rhenium compound to the oxide. Temperatures in the range of about 350 C. to about 800 C. are generally satisfactory for such calcination.

The proportion of the rhenium oxide (rhenium heptoxide) combined with the support can vary appreciably but generally the support will contain at least 0.1 percent by weight of rhenium oxide with amounts from 0.2 to about 40 percent by weight being preferred and about 2 to about 20 percent by weight especially preferred. The weight percent referred to is based on the combined weights of the support and the rhenium oxide.

The rhenium oxide catalyst is combined with a promoting amount of an aluminum alkyl compound of the formula $AlR_3$ wherein each R independently can range from 1 to about 6 carbon atoms. Representative examples of suitable aluminum alkyl compounds include trimethylaluminum, triethylaluminum, tributylaluminum, trihexylaluminum, and the like, as well as mixtures thereof.

The amount of promoting aluminum alkyl employed can vary depending upon the level of activation desired. Generally the aluminum alkyl will be employed in an amount in the range of about 1 to about 100, preferably about 5–40 weight percent based on the total weight of the rhenium oxide catalyst prior to the addition of the aluminum alkyl.

The aluminum alkyl can be combined with the rhenium catalyst in any suitable manner. The aluminum alkyl is preferably contacted with the rhenium oxide catalyst in a hydrocarbon diluent and can be applied to the rhenium catalyst by spraying, immersing, or other liquid treatment.

It is essential that the combination of the aluminum alkyl and the rhenium catalyst be heated to an elevated temperature sufficient to cause the promotion to take place. Generally this involves heating the catalyst to at least 200° C. The length of time of heating the catalyst composite is generally in the range of about 15 minutes to about 24 hours. It is accordingly currently preferred to apply the aluminum alkyl to a bed of the rhenium catalyst and then flow a suitable oxygen-containing gas, such as air, through the bed at a temperature in the range of about 350° C. to about 800° C. for a length of time sufficient to activate the catalyst. Typically less time is required at higher temperatures and vice-versa. If desired, the thus calcined catalyst can be further treated with an inert gas such as nitrogen prior to use in the disproportionation reaction.

In accordance with a further embodiment of the invention an aluminum alkyl promoted rhenium oxide catalyst after calcination can be additionally promoted by incorporation of a tin alkyl, such as tetramethyl tin. Suitable tin alkyl compounds of the formula $SnR_4$ that can be used include those with each R independently having from 1 to about 6 carbon atoms such as tetramethyl tin, tetraethyl tin, tetrabutyl tin, tetrahexyl tin, and the like, and mixtures thereof.

The amount of promoting tin alkyl employed can vary depending upon the level of activation desired. Generally a tin alkyl will be employed in an amount of 0.5 to about 100, preferably 1–40, weight percent based on the total weight of rhenium oxide catalyst prior to the addition of the tin alkyl.

The tin alkyl can be combined with the rhenium oxide catalyst in any suitable manner. One preferred mode of combining tin alkyl with the rhenium catalyst is to contact the catalyst with a hydrocarbon solution of the tin alkyl. Following contact with a bed of the catalyst, for example in the reactor, the solvent can be removed by stripping with suitable gas flow or otherwise treating. The catalyst is then immediately suitable for use in the disproportionation reaction.

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3–30 carbon atoms per molecule and with such cyclic olefins having 4–30 carbon atoms per molecule. Nontertiary olefins are those olefins wherein each carbon atom, which is attached to another carbon atom by means of a double bond, is also attached to at least one hydrogen atom.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexane, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclododecatriene, 1,4,7,10-cyclododecatetraene, 6-methyl-6-ethylcyclooctadiene-1,4, and the like, and mixtures thereof.

The reaction temperature can vary depending upon the catalyst and feed(s) employed. Typically the disproportionation is carried out at a temperature in the range of about 0° to about 300° C., preferably from about 20° to about 150° C.

The disproportionation reaction can be carried out by contacting the olefins to be disproportionated with the catalyst in the liquid phase or the gas phase depending on structure and molecular weight of the olefin. Pressure during the disproportionation reaction can vary between wide limits. For example, pressures between 0.1 and 500 atmospheres are suitable, although preferred pressures are between about 1 and 40 atmospheres.

If the reaction is carried out in the liquid phase, solvents or diluents for the reactants can be used. Aliphatic saturated hydrocarbons e.g., pentane, hexanes and cyclohexane, dodecane and aromatic hydrocarbons such as benzene and toluene are suitable. If the reaction is carried out in the gaseous phase diluents such as aliphatic hydrocarbons for example, methane, ethane, and or substantially inert gases, e.g. nitrogen, argon, can be present. Preferably, the disproportionation reaction is effected in the absence of significant amounts of deactivating materials such as water and oxygen.

The contact time needed to obtain a reasonable yield of disproportionated products depends upon several factors such as the activity of the catalyst, temperature, pressure and structure of the olefinically unsaturated compound to be disproportionated. Length of time during which the olefinic unsaturated compounds to be disproportionated are contacted with the catalyst can conveniently vary between 0.1 seconds and 24 hours although longer and shorter contact times can be used. Preferably, times of about 1 second to about 1 hour are used.

The process of the invention can be effected batchwise or continuously with fixed bed catalyst beds, slurried catalyst, fluidized beds, or by using any other conventional contacting techniques.

A further understanding of the present invention and its advantages will be provided by reference to the following examples.

All runs were made by passing a propylene feed through a stainless steel pipe vertical tubular reactor (½ inch diameter by 25 cm length) positioned in a temperature-controlled electric furnace. In each run the reactor contained a bed of the designated catalyst. A thermocouple was positioned in the catalyst bed to monitor reaction temperature.

The propylene feed was of a polymerization grade as sold by Phillips Petroleum Company of Bartlesville, Okla. The propylene feed was pretreated with activated Alcoa H151 alumina and activated magnesia prior to metathesis. The feed was passed downwardly through the vertically oriented tubular reactor.

Reaction product analysis was made by gas-liquid chromatography (glc) employing a Hewlett-Packard model 5880A chromatograph having a ⅛ inch by 20 ft. column packed with 19% bis-2-methoxyethoxyethylene (BMEE) +1% squalene on 60/80 Chrom. P. Analysis was carried out isothermally at a temperature of about 30° to 40° C. with a helium carrier gas flow rate of about 20 mL/min.

EXAMPLE I

Five different catalyst compositions were prepared to be tested for propylene metathesis.

Control catalyst A was prepared by adding a solution containing 3.6 g ammonium perrhenate in 35 mL of water to 30 g of titanium dioxide powder. The resulting slurry was dried on a hot plate with constant stirring. A 5.0 g portion of −20+60 mesh catalyst was placed in the reactor and activated by heating at 550° C. for 60 minutes in flowing dry air, then for 30 minutes in dry nitrogen. The rhenium content of catalyst A was calculated to be 10.8 wt % rhenium heptoxide. After cooling to 40° C. it was ready to metathesize propylene.

Control catalyst B was prepared starting with 5.0 g of catalyst A that had been activated as described above. After cooling under nitrogen to room temperature the catalyst was transferred, under nitrogen, to a flask. After evacuation of the flask the catalyst was sprayed with 5 mL of a solution of 25% tetramethyltin in cyclohexane. Solvent was removed by evacuation and the catalyst, under a nitrogen atmosphere, was transferred to the reactor. After warming to 40° C., the catalyst which contained 20 wt % tetramethyltin on catalyst A was ready to metathesize propylene.

Preparation of control catalyst C was identical to that of catalyst B except that the activated and cooled catalyst was sprayed with 5.8 mL of a solution of 25% triethylaluminum in n-hexane. After removal of solvent by evacuation, catalyst C was calculated to contain 20 wt % triethylaluminum on catalyst A.

Invention catalyst D was obtained by activating the composition of catalyst C in the reactor at 550° C. for 60 minutes in flowing dry air, then for 30 minutes in dry nitrogen.

Invention catalyst E was prepared by addition of tetramethyltin to catalyst D. The procedure used was identical to that described for the preparation of catalyst B. After removal of solvent by evacuation, catalyst E was placed in the reactor, warmed to 40° C., and ready to metathesize propylene.

EXAMPLE II

The catalysts prepared as described above were tested for propylene metathesis activity at a temperature of 40° C., pressure of 75 psig and a propylene feed rate of 4 weight hourly space velocity (WHSV). In all runs, 5.0 grams of catalyst were employed. Conversion of propylene feed to ethylene plus butenes was determined by glc, and is summarized in the Table.

TABLE

| Catalyst | Propylene Conversion, % time, minutes | | | |
|---|---|---|---|---|
| | 5 | 30 | 60 | 120 |
| A | 5.6 | 0.3 | — | — |
| B | tr. | tr. | — | — |
| C | 0.8 | 0.3 | 0.3 | — |
| D (Invention) | 22.4 | 15.9 | 12.6 | — |
| E (Invention) | 35.3 | 35.8 | 35.8 | 33.7 |

The results of these experiments demonstrate the increased catalyst activity achieved upon catalyst treatment with triethylaluminum followed by activation in dry air at 550° C. Additional catalyst activation is observed upon further treatment of the inventive catalyst with tetramethyltin, while direct treatment of $Re_2O_7$—$TiO_2$ catalyst with tetramethyltin (catalyst B) appeared to be detrimental to catalyst metathesis activity.

What is claimed is:

1. A process for disproportionating olefins which comprises contacting at least one feed olefin having at least 3 carbon atoms per molecule under reaction conditions with a catalytic amount of a catalyst composition produced by contacting an inorganic refractory oxide containing rhenium oxide and a promoting amount of at least one aluminum alkyl compound and subjecting same to conditions suitable for said aluminum alkyl to promote the activity of said rhenium oxide for the disproportionation reaction.

2. A process according to claim 1 wherein said aluminum alkyl is triethylaluminum.

3. A process according to claim 1 wherein the amount of aluminum alkyl employed ranges from about 1 to about 100 weight percent of the combined weights of rhenium oxide and inorganic refractory oxide.

4. A process according to claim 3 wherein the inorganic oxide comprises titanium dioxide.

5. A process according to claim 1 wherein said conditions comprise thermal treatment at a temperature of at least about 200° C. in the presence of an oxygen-containing gas.

6. A process according to claim 1 wherein the catalyst additionally contains a promoting amount of at least one tin alkyl compound.

7. A process according to claim 6 wherein said tin alkyl is tetramethyl tin.

8. A process according to claim 6 wherein the amount of tin alkyl present in the catalyst ranges from about 0.5 to about 100 weight percent of the combined weight of rhenium oxide catalyst prior to addition of tin alkyl.

9. A process according to claim 1 wherein the catalyst is rhenium heptoxide on titanium dioxide promoted with triethylaluminum which is activated by thermal treatment at a temperature of at least about 200° C. with air.

10. A process according to claim 9 wherein the catalyst additionally contains tetramethyl tin.

11. A process for disproportionating olefins which comprises contacting at least one feed olefin having at least 3 carbon atoms per molecule under reaction conditions with a catalytic amount of a catalyst composition produced by contacting an inorganic refractory oxide containing rhenium oxide with a promoting amount in the range of about 1 to about 100 weight percent based on total weight of rhenium oxide catalyst of at least one aluminum alkyl compound of the formula $AlR_3$ wherein each R independently can range from 1 to about 6 carbon atoms and subjecting the composition thus-produced to elevated temperature conditions of at least about 200° C. and of an oxygen-containing gas to promote the activity of said rhenium catalyst oxide for the disproportionation reaction.

12. A process according to claim 1 wherein said aluminum alkyl is triethylaluminum.

13. A process according to claim 11 wherein the inorganic oxide comprises titanium dioxide.

14. A process according to claim 11 wherein the catalyst additionally contains a promoting amount of at least one tin alkyl compound of the formula $SnR_4$ wherein each R independently can range from 1 to about 6 carbon atoms and wherein said amount ranges from about 0.5 to about 100 percent based on total weight of rhenium oxide catalyst prior to addition of the tin alkyl.

15. A process according to claim 14 wherein said tin alkyl is tetramethyl tin.

16. A process according to claim 14 wherein the catalyst is rhenium heptoxide on titanium dioxide promoted with triethlaluminum and tetramethyl tin.

* * * * *